United States Patent
Young et al.

(10) Patent No.: US 9,398,929 B2
(45) Date of Patent: Jul. 26, 2016

(54) PIN IMPACTOR

(75) Inventors: Duncan Young, Hebden Bridge (GB); Dean Cowan, Huddersfield (GB)

(73) Assignee: DEPUY (IRELAND), Cork (IE)

( * ) Notice: Subject to any disclaimer, the term of this patent is extended or adjusted under 35 U.S.C. 154(b) by 447 days.

(21) Appl. No.: 13/885,137

(22) PCT Filed: Nov. 11, 2011

(86) PCT No.: PCT/GB2011/052207
§ 371 (c)(1),
(2), (4) Date: Jul. 23, 2013

(87) PCT Pub. No.: WO2012/063083
PCT Pub. Date: May 18, 2012

(65) Prior Publication Data
US 2013/0296875 A1    Nov. 7, 2013

(30) Foreign Application Priority Data

Nov. 12, 2010  (GB) .................................. 1019154.2

(51) Int. Cl.
*A61B 17/92*  (2006.01)

(52) U.S. Cl.
CPC ............ *A61B 17/92* (2013.01); *A61B 2017/922* (2013.01)

(58) Field of Classification Search
USPC ....................................... 81/44; 433/121, 150
See application file for complete search history.

(56) References Cited

U.S. PATENT DOCUMENTS

| | | | | |
|---|---|---|---|---|
| 1,387,316 A | * | 8/1921 | Schmidt ..................... | B25F 1/00 7/169 |
| 1,440,072 A | * | 12/1922 | Greener .................... | B25C 9/00 81/44 |
| 2,341,375 A | * | 2/1944 | Hambleton ............. | B25B 23/18 362/119 |
| 2,432,967 A | * | 12/1947 | Johnson .................... | B41J 11/27 226/81 |
| 2,481,209 A | * | 9/1949 | Farnsworth ............ | A45D 8/185 132/330 |
| 2,716,406 A | * | 8/1955 | Borella ............... | A61B 17/1717 606/104 |
| 2,824,651 A | * | 2/1958 | Davis ....................... | A61C 3/04 211/69 |

(Continued)

FOREIGN PATENT DOCUMENTS

| EP | 463551 A1 | 1/1992 |
|---|---|---|
| EP | 1090591 A2 | 4/2001 |

(Continued)

OTHER PUBLICATIONS

English translation of JP 8308676.*

(Continued)

*Primary Examiner* — Christian Sevilla

(57) ABSTRACT

A multi-pin pin impactor and method of use are described. The pin impactor includes a body which can be held by a user and manipulated to re-position the pin impactor during use. First and second pin holders are attached to the body and each include a pin release mechanism effective to releasably retain a pin within the pin holder. An impaction can have a force applied to apply a driving force to a one of the pins. In use, a first pin held by the pin impactor is introduced into an aperture in a surgical instrument mounted on a bone. A force is applied to the pin impactor to drive the first pin into the bone. The orientation or position of the pin impactor is changed to introduce a second pin held by the pin impactor into a second aperture in the surgical instrument without re-loading the pin impactor and a force is applied to the pin impactor to drive the second pin into the bone.

7 Claims, 4 Drawing Sheets

(56) References Cited

U.S. PATENT DOCUMENTS

| | | | | |
|---|---|---|---|---|
| 2,870,809 | A * | 1/1959 | Feldman | B25G 1/005 81/177.5 |
| 3,561,510 | A * | 2/1971 | Johnson | B25G 1/005 81/177.5 |
| 3,847,193 | A * | 11/1974 | Brunstetter | B25C 3/006 227/147 |
| 3,879,848 | A * | 4/1975 | Murphy | B25D 5/00 30/359 |
| 4,037,592 | A * | 7/1977 | Kronner | A61B 17/1703 606/97 |
| 4,349,018 | A * | 9/1982 | Chambers | A61B 17/15 30/293 |
| 4,354,540 | A * | 10/1982 | Jefferson | B25B 23/10 81/44 |
| 5,020,398 | A * | 6/1991 | Leu | B25B 13/005 81/124.4 |
| 5,098,235 | A * | 3/1992 | Svetlik | B25H 3/003 206/379 |
| 5,425,490 | A * | 6/1995 | Goble | A61B 17/0642 227/147 |
| 5,664,274 | A * | 9/1997 | Collins | B25F 1/003 224/904 |
| 6,345,554 | B1 * | 2/2002 | Wang | B25B 23/0035 81/124.4 |
| 6,953,114 | B2 * | 10/2005 | Wang | B25H 3/003 206/372 |
| 2003/0110900 | A1 * | 6/2003 | Chen | B25C 3/008 81/44 |
| 2007/0233156 | A1 * | 10/2007 | Metzger | A61B 17/155 606/130 |
| 2008/0087443 | A1 * | 4/2008 | Jemail | A01L 11/00 168/48.1 |
| 2013/0261681 | A1 * | 10/2013 | Bittenson | A61F 2/4603 606/86 R |

FOREIGN PATENT DOCUMENTS

| | | | |
|---|---|---|---|
| JP | 8309676 | * | 11/1996 |
| JP | 8309676 | A | 11/1996 |
| WO | WO 2010121028 | A2 | 10/2010 |

OTHER PUBLICATIONS

PCT International Search Report PCT/GB2011/052207 dated May 11, 2012.

UK Search Report GB 1019154.2 dated Feb. 24, 2011.

* cited by examiner

PIN IMPACTOR

CROSS REFERENCE TO RELATED APPLICATION

This application is a National Stage 35 U.S.C. 371 of International Patent Application PCT/GB2011/052207 filed Nov. 11, 2011.

BACKGROUND OF THE INVENTION

The present invention relates to surgical instruments, and in particular to a pin impactor and method of use thereof.

In surgical procedures, pins can be used to locate instrumentation on a bone. For example, during a knee replacement procedure, a femoral cutting block can be placed on the anterior, distal part of the femur adjacent the condyles and held in position by placing pins through a number of apertures in the cutting block and then driving the pins into the bone to prevent the cutting block from moving. Once the position of the cutting block is stabilised using the pins, the secondary fixing means, such as bone screws, can also be used to more securely attach the cutting block to the bone.

Typically at least two, or more, pins are used to fix the position of the instrument as otherwise the instrument can pivot about a single pin. An existing pin impactor can hold a single pin and is used twice to place two pins to fix a cutting block. However, this involves the surgeon using the pin impactor a first time to impact a first pin, and then the pin impactor being reloaded with a second pin, either by the surgeon or by somebody attending surgery, and then being used again to impact the second pin.

However, having to re-load the pin impactor introduces delays and difficulties into surgery. The re-loading of the pin impactor generally adds steps to the surgical procedure. If the surgeon, reloads the pin impactor, then he has to let go of the instrument being fixed, which may then move and therefore needs careful re-positioning before impacting the second pin.

If the pin impactor is reloaded by another person, then the surgeon can pass the pin impactor to them for reloading and then wait for it to be re-loaded and passed back, again adding delays and more handling of sharps, as the pin tip is sharp. Alternatively, the surgeon can hold the empty pin impactor, while another person places a second pin in the impactor, but that can be a very fiddly manual activity as the pins can have small diameters and again requires the handling of sharps and so is potentially dangerous.

An alternative is simply to have multiple pin impactors each pre-loaded with a single pin, but that again introduces delays as each pin impactor is passed to and from the surgeon and also introduces more sharps and more sharps handling and also adds more instrumentation to an area already full of instruments.

It would therefore be beneficial to be able to more quickly, safely and easily allow more than one pin to be impacted by a surgeon.

The invention provides a multi-pin pin impactor which can be used by a surgeon to impact more than one pin, without requiring re-loading with pins.

BRIEF SUMMARY OF THE INVENTION

According to a first aspect of the present invention, there is provided a multi-pin pin impactor, comprising: a body holdable by a user and manipulable by the user to re-position the pin impactor during use; a first pin holder attached to the body and including a first pin release mechanism effective to releasably retain a first pin within the first pin holder; a second pin holder attached to the body and including a second pin release mechanism effective to releasably retain a second pin within the second pin holder; and an impaction portion, by which a force can be applied to the multi-pin pin impactor to apply a driving force to one of the pins.

As the pin impactor can hold multiple pins in a releasable fashion, there is no need to re-load the pin impactor during use and so the number of steps is reduced, making surgery quicker, and also sharps handling is reduced making the risk of injury or glove damage less.

The pin impactor can include more than two pin holders. For example, the pin impactor can include three, four, five or more pin holders. Each pin holder can have the same or similar general construction. The pin impactor can comprise a further, or a plurality of further pin holders, each further pin holder including a pin release mechanism effective to releasably retain a pin within the pin holder. Hence, the pin impactor can be used to impact more than two pins, if needed to fix a piece of instrumentation or to fix more than one piece of instrumentation.

The pin impactor can be configured or can have a geometry to help reduce the chance of fouling of the pin impactor in use. The orientations of the first pin holder and the second pin holder can prevent fouling of the pin holder in use. The configuration or geometry of the pin impactor can be such that when the pin impactor is being used to impact a first pin, the second pin and any other pins do not foul against other instrumentation or the patient's bone.

The first pin holder can have a first longitudinal axis and the second pin holder can have a second longitudinal axis. The angle subtended by the first longitudinal axis and the second longitudinal axis can be between approximately 180° and 30°. The angle can be between approximately 180° and 120° The angle can be between approximately 120° and 45°. More preferably, the angle is between approximately 90° and 45°. The angle can be an obtuse angle or an acute angel, but preferably the angle is an acute angle. Most preferably the angle is approximately 60° or approximately 120°, the latter making the pin holder particularly suitable for use, for example, in minimally invasive procedures. The angle can be greater than approximately 30°. The angle between each adjacent pair of pin holders can be substantially the same.

The pin impactor can have a plurality of separate limbs. Each limb can provide either a pin holder or an impaction surface. An impaction surface can be provided at an opposite end of a limb providing an associated pin holder.

All of the pin holders can lie in a common plane. Hence, the pin impactor has a generally planar star shaped configuration.

All of the pin holders may not lie in a common plane. Hence, the pin impactor has a more three dimensional configuration. The longitudinal axes of the pin holders may lie on the vertices of a generally pyramidal shape.

The impaction portion can be a single impaction surface. The impaction surface can have different regions oriented in different directions so as to direct an impaction force toward a corresponding associated pin holder.

The impaction portion can include a separate impaction surface for each pin holder. The plane of each impaction surface can be generally perpendicular to the longitudinal axis of an associated pin holder.

The pin impactor can have a composite construction. The pin impactor can comprise a core of a first material. The pin impactor can comprise a coating disposed over at least a portion of the core. The coating can be of a second material which is different to the first material. The first material can be a load bearing material suitable to transmit an impaction force to a pin held by the impactor. The first material can be a rigid material.

The first material can be a plastic, and in particular a polymer. Suitable plastics for reusable pin holders include, for example PEEK, PAEK and PPSU. Suitable plastics for single use or disposable pin holders include, for example, PA66, POM, PC, ABS, PP, PARA. The plastic or polymer material can be fibre-reinforced, so as to provide extra rigidity, for example glass-fibre reinforced.

The first material can be a metal or alloy, such as stainless steel, titanium, aluminium, cobalt-chrome, brass or alloys including such metals. For single use or disposable pin holders, the metal can be steel, such as mild steel or carbon steel. The second material can provide a grip. The second material can be a resilient material such as a rubber or a plastic. The second material can be less rigid than the first material. The coating can be moulded over the core. The core can have a unitary construction or can be made from a plurality of core members. Each core member can have a generally similar construction.

Each pin release mechanism can include a friction fit part. The friction fit part can provide sufficient friction to prevent a pin falling out of the pin holder under the action of gravity, vibration or momentum of the pin itself during handling of the pin holder, but allows the pin to be released from the pin holder when held in bone. The friction fit part can include an O-ring. The O-ring can be a rubber O-ring.

The invention can also be provided as a kit of parts comprising a pin impactor according to the first aspect of the invention and at least two pins or a pin for each pin holder of the pin impactor.

The invention can also be provided as an assembly comprising a pin holder according to the first aspect of the invention and a pin located in each pin holder of the pin impactor.

According to a second aspect of the present invention, there is provided a method of pinning a surgical instrument to a bone using a multi-pin pin impactor holding at least two pins comprising: introducing a first pin held by the pin impactor into an aperture or mounting formation of the surgical instrument mounted on a bone; applying a force to the pin impactor to drive the first pin into the bone; changing the orientation and/or position of the pin impactor and introducing a second pin held by the pin impactor into a second aperture or mounting formation of the surgical instrument without re-loading the pin impactor; and applying a force to the pin impactor to drive the second pin into the bone.

Hence, there is no need to re-load the pin impactor during use. The surgeon merely re-positions and/or re-orients the pin impactor in order to allows a second pin to be driven into bone to fix instrumentation. Therefore, the number of steps is reduced, making surgery quicker, and also sharps handling is reduced making the risk of injury or glove damage less.

BRIEF DESCRIPTION OF THE DRAWINGS.

An embodiment of the invention will now be described, by way of example only, and with reference to the accompanying drawings, in which.

Figure 1:
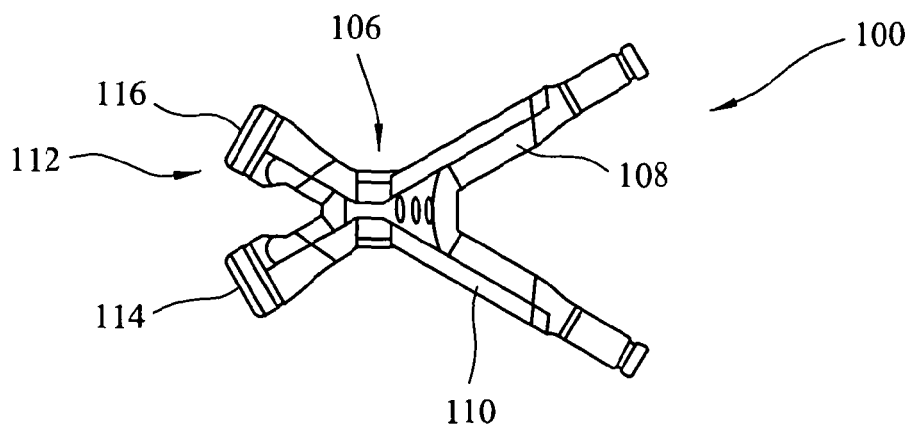
FIG. 1 shows a side view of a pin impactor according to the invention.

Similar items in different Figures share common reference numerals unless indicated otherwise.

DETAILED DESCRIPTION OF THE INVENTION

Figure 2:
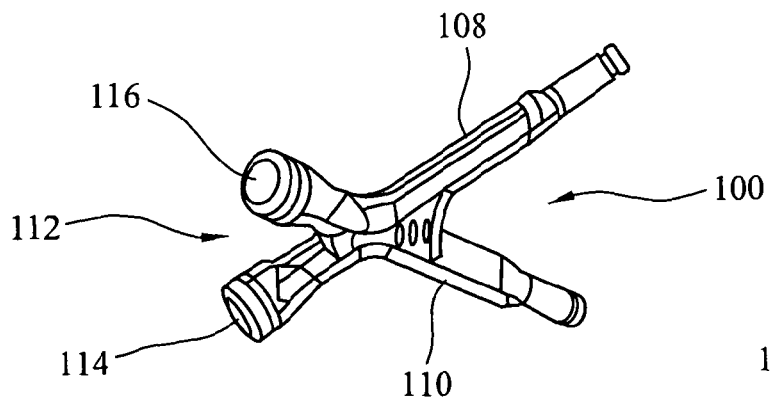
FIG. 2 shows a perspective view of the pin impactor shown in FIG. 1.
Figure 3:
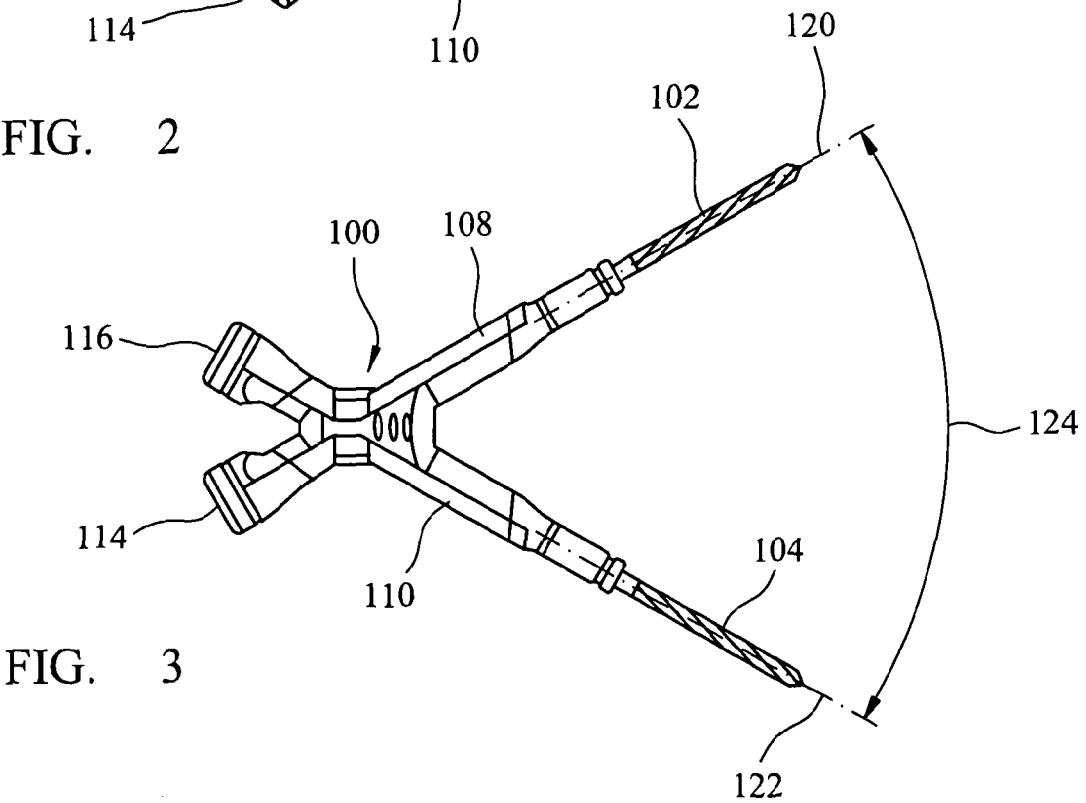
FIG. 3 shows a side view of the pin impactor shown in FIGS. 1 & 2 and loaded with two pins.

With reference to FIG. 1, there is shown a side view, a multi-pin pin impactor 100 according to the present invention. FIG. 2 shows a perspective view of the pin impactor 100 from the rear. FIG. 3 shows a side view of an assembly comprising the pin impactor 100 loaded with a first pin 102 and a second pin 104 as will be described in greater detail below.

As illustrated in FIG. 1, the pin impactor 100 includes a body portion 106 from which a first pin holder 108 and a second pin holder 110 extend. The pin impactor 100 also includes an impacted portion 112 disposed on a generally opposite side of the pin impactor to the pin holders. The impaction portion includes a first impaction surface 114 associated with the first pin holder 108, and a second impaction surface 116 associated with the second pin holder 110.

As illustrated in FIGS. 1 to 3, the pin impactor has a generally 'X' shape and the pin holders lie in a common plane. As illustrated in FIG. 3, the first pin holder 108 has a first longitudinal axis 120 associated with it and the second pin holder 110 has a second longitudinal axis 122 associated with it. The angles attended by the longitudinal axis of the pin holders is approximately 60° as illustrated by line 124.

Figure 4:
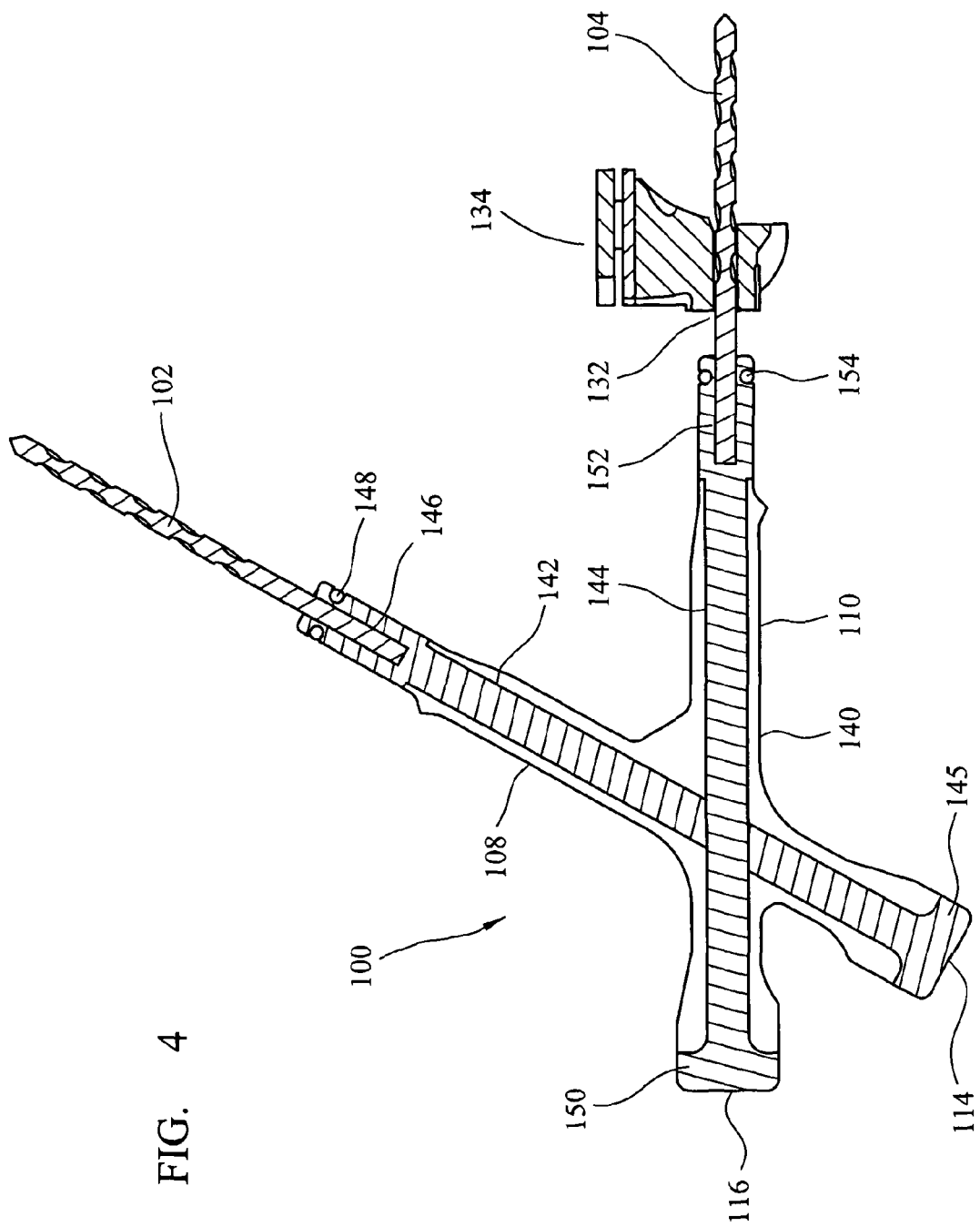
FIG. 4 shows a cross sectional view of the loaded pin impactor in use with a cutting block.

The construction of the multi-pin pin impactor 100 is illustrated in greater detail in FIG. 4 which shows a cross section through the central plane of the pin impactor 100. FIG. 4 illustrates the pin impactor in use wherein the second pin 104 is passing through an aperture 130 in a cutting guide block 134. As illustrated in FIG. 4, the pin impactor 100 has a composite structure and is made from at least two different materials. The pin impactor has a core structure which provides mechanical strength and also an outer coating of a second material 140, softer than the material of the core structure. The outer coating 140 helps to hold the core structure together and also provides grip to a user of the pin impactor.

The core of the impactor comprises similar first and second members 142, 144 of similar construction. First core member 142 has a generally circular cylindrical construction and includes a head part 144 at a proximal end and a circular cylindrical cavity 146 at a second distal end which receives and can releasably retain a proximal end of pin 102 in use. A pin release mechanism is provided by a rubber O-ring located in an annular channel extending around the outer surface of the distal end of core member 142. O-ring 148 provides a friction fit exerting sufficient force on the small end of the pin such that the pin is retained in the pin holder during normal use. That is, the frictional force is sufficient to prevent the pin falling out of the pin holder and so the pin impactor can be manipulated and handled by a surgeon without the pin falling out. The second core member 144 has a similar construction and also comprises a head 150 at a proximal end, a circular cavity 152 at a distal end and an over O-ring 154 at a distal end located in an annular cavity extending around the pin holder. Similarly, O-ring 154 acts as part of a friction fit mechanism to retain pin 104 within cavity 152 to prevent it falling out under action of gravity, vibration, momentum or other forces that the pin might experience while the pin impactor is being handled by a surgeon.

A middle portion of each core member 142, 144 includes a notch allowing the core members to be assembled in the 'X' configuration shown in FIG. 4 in which the notch of each core member receives the remaining part of the other core member.

As illustrated in FIG. 4, the core members are made of a metal, such as 17-14 stainless steel. The outer coating 140 can be a 50 shore silicon rubber over-molded using gum transfer or liquid silicon rubber injection, on to the metal core.

Figure 5:
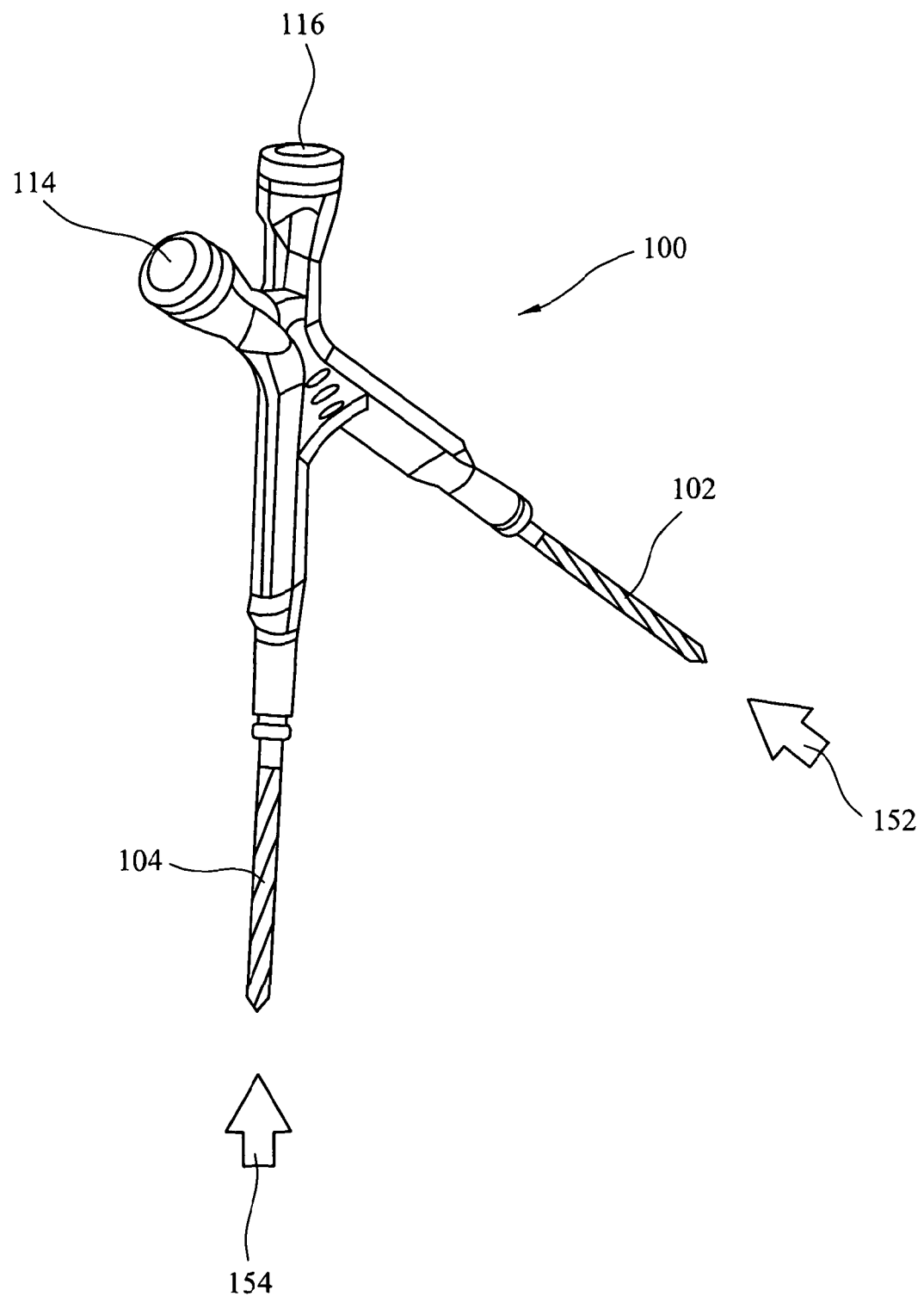
FIG. 5 illustrates a first loading part of a method of use of the pin impactor according to the invention.

Use of the pin impactor will now be described with reference to FIGS. 5 to 7. Initially, as illustrated in FIG. 5, the multi-pin impactor 100 is loaded with the first pin 102 and second pin 104 by manually inserting and pushing, in the direction illustrated by arrows 150 and 152 respectively, into the cavities 146 and 152 of the pin holders. Some force is required in order to overcome the friction caused by the O-rings 148, 154. Once inserted, the pins are retained within the pin holders by the frictional force of the O-rings acting on the outer surface of the pins. Although threaded pins are illustrated in the figures, it will be appreciated that any kind of impactable pin can be used in practice. For example, the pins can be Steinmann pins. As will be appreciated in the art, the diameter of impactable pins is typically in the region of a few millimetres and they often have a sharp tip, such as a trochar tip, allowing their impaction into bone.

Figure 6:
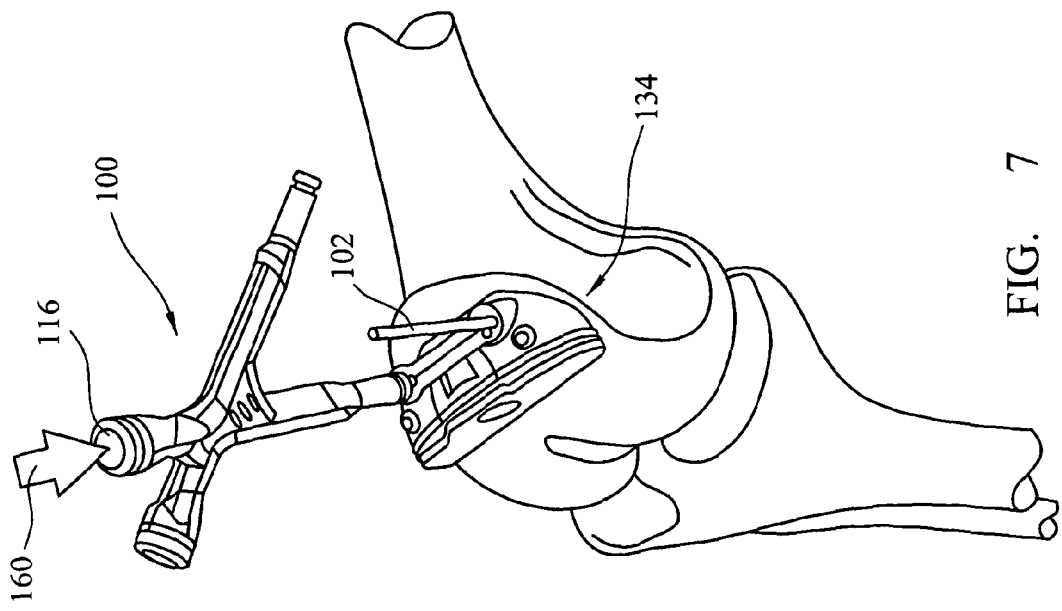
FIG. 6 illustrates impacting a first pin during a method of use of the pin impactor.
Figure 7:
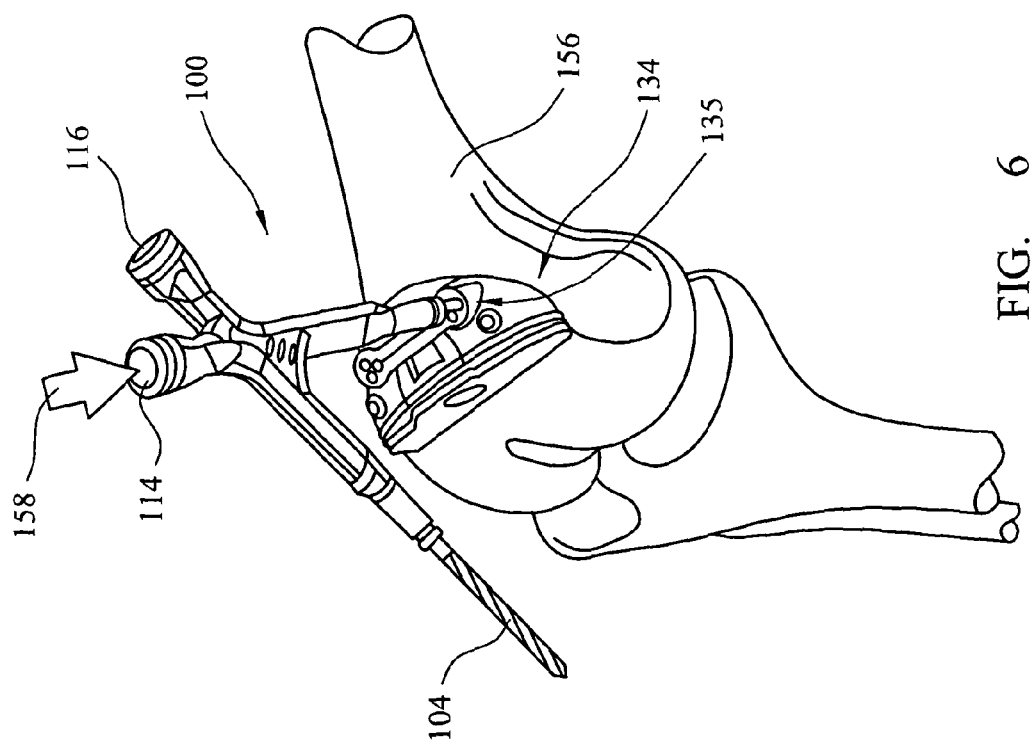
FIG. 7 illustrates impacting a second pin during a method of use of the pin impactor.

FIG. 6 shows a femoral cutting block 134 located on the anterior surface of a femur 156 near the condyles. The cutting block 134 includes a first group of three apertures 135 and a second group of three apertures 136 for receiving bone pins to fix the cutting block 134 on the patient's bone 156.

As illustrated in FIG. 6, the first bone pin 102 is introduced into a one of the fixing apertures 135 of cutting block 134 by the surgeon holding and manipulating the body portion of the pin impactor 100. An impaction force, illustrated by arrow 158 is then applied to the first impaction surface 114, e.g. by the surgeon striking impaction surface 114 with a mallet or similar tool, so as to drive pin 102 into the patient's bone. As is illustrated in FIG. 4, by striking impaction surface 114, an impaction force is transmitted along the body of the first core element 142 on to the proximal end of the pin 102 so as to drive the sharp distal end of the pin 102 into the patient's bone. The pin impactor 100 is then pulled away from and along the longitudinal axis of the pin. The force retaining the pin in the bone is sufficient to overcome the frictional force exerted by O-ring 148 and so the pin is released from the pin impactor and is retained in the patient's bone as illustrated in FIG. 7.

The surgeon then manually repositions the pin impactor above an appropriate one of the second group of apertures 136 of the cutting block 134 and inserts the second pin 104 into the selected aperture. Then, as illustrated in FIG. 7, an impaction force, illustrated by arrow 160 is applied to the second impaction surface 116 so as to drive the second pin 104 into the bone of the patient. The pin impactor is then withdrawn over the proximal end of pin 104 and again the retaining force of the bone acting on the distal end of the pin is sufficient to overcome the frictional force of O-ring 154 so that the pin 104 is released from the pin impactor and retained in the patient's bone. The two pins 102, 104 therefore fix the cutting block 134 at the appropriate position on the femur.

If necessary, further fixing pins can also be inserted and any further fixing means, such as bone screws or similar can also be used to more securely fix the cutting block to the patient's bone, if required. It will be appreciated that the invention is not limited to the use of bone pins for fixing cutting blocks. Rather, the invention can be used with any instrumentation with which pins are commonly used to fix the instrumentation's position on bone.

It will be appreciated that there are a number of advantages associated with the multi-pin pin impactor of the invention. The pin impactor is of simple construction and has no moving parts. The pin impactor reduces the number of steps that a surgeon needs to carry out when fixing instrumentation using pins and therefore can speed up the surgical process. Further, it improves the safety of a surgical process as there is reduced handling of sharps.

It will be appreciated that various modifications can be made to the pin impactor shown in the figures. For example, the pin impactor can include more than two pin holders. For example, the pin impactor can include three, four or more pin holders. The pin holders can be arranged in a common plane such that the pin impactor has a generally planar star like configuration. Alternatively, in other embodiments, the pin holders may not lie in a common plane and so the pin impactor will take on the configuration of a tripod and correspondingly higher number of limbs, depending on the number of pin holders. However, a benefit of the planar pin holder configuration is that reusable embodiments are easier to reprocess or wash using dishwasher type decontamination machines, than the non-planar, more three-dimensional configurations.

The composite construction of the pin holder provides a number of advantages. The core of the pin impactor provides the mechanical strength required in order to transmit the impaction force from the impaction surface to the pin. The coating material 140 improves the grip of the pin impactor so that it is easier for the surgeon to manipulate the pin impactor in use. As will be appreciated, surgical procedures often result in instrumentation being coated in blood or other body fluids which can make them slippery. Hence, a coating material 140 is used to provide improved grip, compared to a bare metal surface.

Further, the geometry or configuration of the pin impactor is selected to try and minimise fouling of the instrument in use. For example, as illustrated in FIGS. 3 and 6, the pins subtend an angle of approximately 60°. This helps to ensure that when a first pin is inserted in the instrumentation, as illustrated in FIG. 6, the second pin 104 is unlikely to foul against the bone or instrumentation being fixed. If the angle were too small, then it is possible that the second pin 104 would foul against the patient's bone or the instrumentation being fixed during use. Hence, the configuration of the pin impactor is designed so as to try and minimise the chance of fouling by providing sufficient clearance for pins held by the pin impactor while other pins are being impacted in use.

It will be appreciated that various modifications and changes to the specific pin impactor will be apparent to the skilled person based from the above discussion and that the invention is not limited only to the above described embodiment of the pin impactor.

The invention claimed is:

1. A multi-pin pin impactor for surgical use with at least a first pin and a second pin, comprising:
   a body holdable by a user;
   a first metal member having an impaction portion at one end, a distal end opposite the impaction portion and a first cavity formed in the distal end, the first cavity sized to receive at least a portion of the first pin;
   a second metal member having an impaction portion at one end, a distal end opposite the impaction portion and a second cavity formed in the distal end, the second cavity sized to receive at least a portion of the second pin; and
   wherein the first member and the second member intersect at a location between the impaction portions and the distal ends;

wherein the first member has a first longitudinal axis and the second member has a second longitudinal axis, and wherein the angle subtended by the first longitudinal axis and the second longitudinal axis is between approximately 30° and 180°;

wherein the impaction portion of the first member includes a first solid impaction surface oriented in one direction to direct an impaction force toward the distal end of the first member and the impaction portion of the second member includes a second solid impaction surface oriented in a different direction to direct an impaction force toward the distal end of the second member;

wherein the first impaction surface is opposite the first cavity and the second impaction surface is opposite the second cavity;

wherein the body comprises an outer non-metallic coating extending over portions of both the first metal member and second metal member while leaving the first impaction surface and second impaction surface exposed; and wherein the body defines open spaces on both sides of the intersection of the first member and second member.

2. The pin impactor of claim 1, wherein the angle subtended by the first longitudinal axis and the second longitudinal axis is approximately 60°.

3. The pin impactor of claim 1, wherein the angle subtended by the first longitudinal axis and the second longitudinal axis is approximately 120°.

4. The pin impactor of claim 1, wherein all of the first member and the second member lie in a common plane.

5. The pin impactor of claim 1, wherein the first metal member and second metal member are discreet components with notches, the first metal member and second metal member are assembled with each notch receiving a portion of the other member at the intersection and wherein the body is molded onto the assembly.

6. The pin impactor of claim 1, wherein the first cavity and the second cavity are sized to form a friction fit with the first pin and the second pin, respectively.

7. A kit of parts comprising the pin impactor of claim 1 and at least a first pin and a second pin.

* * * * *